United States Patent [19]

Grassetti

[11] 4,378,364

[45] Mar. 29, 1983

[54] POSTOPERATIVE TREATMENT OF CARCINOMA PATIENTS

[76] Inventor: Davide R. Grassetti, 26 Northgate Ave., Berkeley, Calif. 94708

[21] Appl. No.: 219,812

[22] Filed: Dec. 22, 1980

Related U.S. Application Data

[63] Continuation-in-part of Ser. No. 923,486, Jul. 10, 1978, abandoned, which is a continuation-in-part of Ser. No. 533,262, Dec. 16, 1974, abandoned, which is a continuation-in-part of Ser. No. 483,894, Dec. 12, 1973, abandoned, which is a continuation of Ser. No. 333,865, Feb. 20, 1973, abandoned, which is a continuation-in-part of Ser. No. 115,758, Feb. 16, 1971, abandoned, which is a continuation-in-part of Ser. No. 34,873, May 5, 1970, abandoned.

[51] Int. Cl.$^3$ ............ A61K 31/455; A61K 31/505; A61K 31/425
[52] U.S. Cl. ................ 424/266; 424/251; 424/270
[58] Field of Search ............. 424/266, 251, 270

[56] References Cited

U.S. PATENT DOCUMENTS 3,698,866  10/1972  Grassetti .................. 23/230 R

OTHER PUBLICATIONS

Chemical Abstracts 70: 95124a, (1969).

*Primary Examiner*—Jerome D. Goldberg

[57] ABSTRACT

Cancer patients following surgery are treated to lessen pain, induce a feeling of well-being and increase appetite by administering to the mammal an effective dosage of a non-toxic dithiobis-heterocyclic compound, belonging to the class of thione-forming disulfides, such as 6,6'-dithiodinicotinic acid (CPDS) which is capable of preferentially reacting with peripheral rather than intracellular sulfhydryl groups. In addition to this blocking effect, treatment with compounds of this type also has the effect of modifying the electric charge of cell surfaces. This blocking of peripheral sulfhydryl groups is not accompanied by toxic effects in laboratory mammals or in man.

5 Claims, No Drawings

POSTOPERATIVE TREATMENT OF CARCINOMA PATIENTS

CROSS REFERENCES TO RELATED APPLICATIONS

The present application is a continuation in part of my application Ser. No. 923,486, filed July 10, 1978, now abandoned, which in turn is a continuation in part of my application Ser. No. 533,262, filed Dec. 16, 1974, now abandoned, which in turn is a continuation in part of my application Ser. No. 483,894, filed Dec. 12, 1973, now abandoned, which in turn is a continuation of application Ser. No. 333,865, filed Feb. 20, 1973, now abandoned, which is a continuation in part of application Ser. No. 115,758, filed Feb. 16, 1971, now abandoned which in turn is a continuation in part of application Ser. No. 34,873, filed May 5, 1970 now abandoned.

SUMMARY OF THE INVENTION

It has been discovered that cellular surface reactions can be modified by bringing the cell into reactive engagement with a reagent which is capable of blocking the sulfhydryl groups of the cell surface.

It has been discovered, more particularly, that cancer patients following surgery are treated to lessen pain, induce a feeling of well-being and increase appetite by administering a non-toxic reagent which is capable of preferentially reacting with peripheral sulfhydryl groups present about mammalian cells rather than with those sulfhydryl groups that are present within the cell. Preferably, the reagent employed is one which, in addition to blocking the peripheral sulfhydryl groups of the cells, also has the effect of modifying the electric charge of the cell surface.

It has been found that various types of dithio compounds, all having the structure R-S-S-R, where R represents an organic radical, have the ability to react preferentially with the peripheral sulfhydryl groups present about the cell.

Those said dithio compounds are dithiobis-heterocyclic compounds and belong to the class of "thione-forming" disulfides. These disulfides wherein the R radicals incorporate groups (such as for example —COOH, —SO$_3$H, or phosphate) which have one or more negative charges under pH conditions of about 7.2 have the ability to modify the electric charge of the cell surface.

Thione-forming disulfides are exemplified by 6,6'-dithiodinicotinic acid

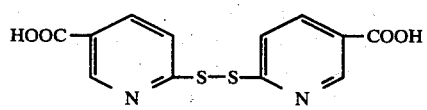

which reacts with thiols or sulfhydryl groups to give an essentially irreversible reaction whose products are a mixed disulfide and a thione.

The pyridine ring used in the example is merely one of the many possible thione-forming disulfides. The main structural requirement for thione-forming disulfides is that they must contain one of the following partial structures, permitting the formation of a thione, as indicated here:

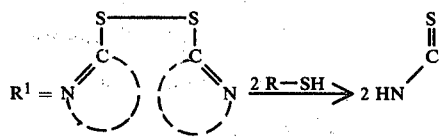

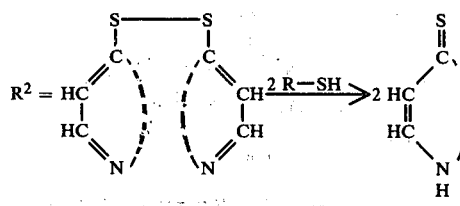

In thione-forming difulfides R-S-S-R the R's may be the same as or different from one another, and they represent heterocyclic radicals containing at least one ring nitrogen atom and optionally sulfur or oxygen in the ring, along with carbon. Said radicals can represent either single or fused rings. Examples of thione-forming disulfides are given in TABLE 1.

For the purpose of the present invention, these rings should preferably bear negative or potentially negative substituents, such as carboxyls, carboxylic esters, amides, sulfonate or phosphate groups or their amide, ester or salt derivatives; or nitro groups (NO$_2$).

TABLE 1
THIONE-FORMING DISULFIDES

Pyridine Derivatives 2,2'-dithiodipyridine
4,4'-dithiodipyridine
6,6'-dithiodinicotinic acid
2,2'-dithiobis-isonicotinic acid
2,2'-dithiobis-(5-aminopyridine)
2,2'-dithiobis-(5-acetamidopyridine)
6,6'-dithiodinicotinamide
2,2'-dithiobis-(5-cyanopyridine)
2,2'-dithiobis-(5-nitropyridine)
2,2'-dithiodipyridine-di-N-oxide

Quinoline Derivatives 2,2'-dithiodiquinoline

Pyrimidine Derivatives 2,2'-dithiodipyrimidine
2,2'-dithiobis-(4-methylpyrimidine)
4-carboxypyrimidine-2-disulfide

Thiazole Derivatives 2,2'-dithiobis-(5'-methylthtazole)
2,2'-dithiobis-benzothiazole
diethyl 2,2'-dithiobis-(4-thiazole carboxylate)

Examples of useful thione-forming disulfides are the following:

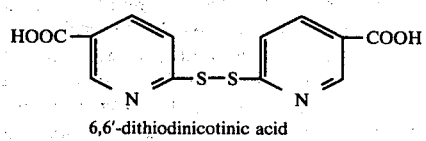

6,6'-dithiodinicotinic acid

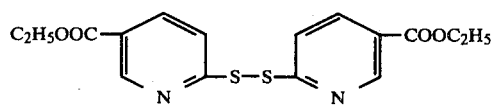

Diethyl Ester of
6,6'-dithiodinicotinic acid

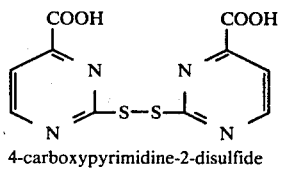

4-carboxypyrimidine-2-disulfide

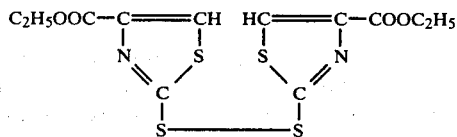

Diethyl 2,2'-dithiobis-(4-thiazole carboxylate)

A typical reaction that takes place between a compound of this class and a peripheral sulfhydryl group on a cell can be presented as follows, when the reaction product not linked to the cell is 6-thiononicotinic acid:

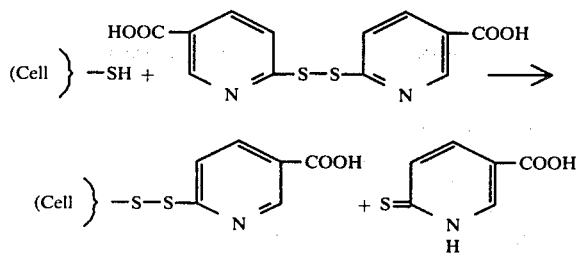

In addition to the exemplary 6,6'-dithiodinicotinic acid reagent referred to above, other representative dithiobis-heterocyclic reagents which have been found to be capable of preferentially reacting with peripheral sulfhydryl groups of cells in the above fashion include:

6,6'-dithiodinicotinic acid diethyl ester
4-carboxypyrimidine-2-disulfide
diethyl 2,2'-dithiobis-(4-thiazole carboxylate)
2,2'-dithiobis-isonicotinic acid together with the sodium salts of said compounds which incorporate carboxyl groups. The latter groups, whether present as such or in salt form, bear a negative charge at a pH of about 7, and thus are capable of modifying the electric charge of the cell which has been treated with these reagents.

The synthesis of these disulfides is often carried out by oxidation of the corresponding thiol with hydrogen peroxide, or iodine-potassium iodide under neutral conditions.

The blocking reaction can be reversed. Thus, when said reaction occurs in the body of a living mammal the blocked groups return to their original —SH form within a relatively short time (usually several hours) as a result of conventional metabolic processes, assuming that no further amounts of the cyclic reagent are available for reaction in the meantime. The administration of a thiol of the type found in mammalian systems such as, for example, glutathione, will also induce restoration of free peripheral —SH groups at a rapid rate. This deblocking reaction, wherein glutathione is indicated by $R^3SH$, can be illustrated as follows using 6,6'-dithiodinicotinic acid as the reagent:

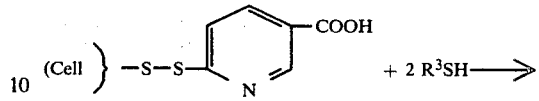

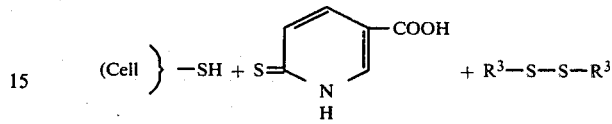

Repeated or continued administration of the thione-forming disulfide to the mammal will, of course, maintain the cellular system in any desired condition of peripheral sulfhydryl group blocking without damage to the cell. This modification of cell membranes may bring about changes in the interaction between cells as well as modification of membrane properties.

In order to determine which of the potentially useful dithiobisheterocyclic compounds or other organic disulfide reagents are capable of preferentially reacting with peripheral cellular sulfhydryl groups, an excess of the reagent can be reacted first with a mass of intact cells and then with a like mass of homogenized, or comminuted cells of the same kind. When the relative amount of the product compound (e.g. thione product) which is formed by reaction with whole cells is very substantially lower than the amount formed during reaction with the homogenate, the desired preferential attribute is present. We have found that this is the case when the dithiobis-heterocyclic compound bears one or more negative, or potentially negative, substituents.

In order to be practical for introduction into a living mammal, it is also necessary that the chemical be non-toxic and cause no harmful impairment of cell metabolism, as determined by its effects on cell glycolysis and respiration. This was found to be the case with CPDS and with 2,2'-dithiobis isonicotinic acid. It was further found that CPDS has no effect on the aggregation of human blood platelets by adenosine diphosphate. Lastly, to make further determinations of toxicity, the chemical can be injected into living mammals at periodic intervals, or it can be administered orally, with the treated animal or individual then being observed for evidence of any abnormal response.

It was found that CPDS, CPDS diethyl ester, and DRG-49 have no toxicity on human subjects, when administered orally at therapeutic doses.

The administration of CPDS to patients with neoplasia and metastases after surgery had a decidedly beneficial effect. In patients receiving CPDS treatment, there is an improvement of their general physical condition, an improvement of their feeling of well-being, and in some cases complete disappearance of the painful syndrome that affected them.

This postoperative treatment usually brought about an increase of appetite as well as an increase of body weight.

EXAMPLE 1

Thione-Forming Disulfides

All the disulfides listed in Table 1 were tested for their ability to form thiones upon reaction with a thiol. They were found to react quantitatively with cysteine to give the corresponding thione. In all cases, formation of the thione caused a large shift of the ultraviolet absorption toward longer wavelengths. The ultraviolet spectrum obtained upon reaction of each disulfide with excess cysteine was identical with that of the thione prepared independently.

EXAMPLE 2

Toxicity of 6,6'-dithiodinicotinic Acid to Mice

The chemical 6,6'-dithiodinicotinic acid was injected into Swiss mice for prolonged periods of time and at high dosage levels to determine whether or not this compound was toxic to mice. The details of this work, together with the results thereof showing non-toxicity, are fully set forth in Table 6.

TABLE 6

TOXICITY OF 6,6'-DITHIODINICOTINIC ACID TO SWISS MICE
INJECTIONS TOTAL DAILY DOSE (mg)

| Number of mice | Number* of daily injections | Dose per injection (mg) | Per mouse (mg) | per kilo (mg) | DURATION OF EXPERIMENT | VISIBLE EFFECT |
|---|---|---|---|---|---|---|
| 6** | 2 | 5 + 12 | 18 | 450 | 21 days | None |
| 13*** | 3 | 4 + 4 + 4 | 12 | 600 | 11 days | None |
| 18**** | 3 | 6 + 6 + 6 | 18 | 900 | 13 days | None |
| 5 | 1 | 20 | 20 | 1,000 | single injection | None |

6,6'-Dithiodinicotinic acid was neutralized with equimolar amount of the Na bicarbonate for injection. The concentration was such that the injected volume was 0.1 ml or 0.2 ml per injection. All injections were intraperitoneal.
*When 2 daily injections were given, the times were 8 AM and 4 PM; when 3 daily injections were given, the times were 8 AM, 12 noon, and 4 PM.
**This group consisted of 40-gram, female Swiss mice. Injections on 21 consecutive days.
***This group consisted of 20-gram, female Swiss mice, 11 females and 2 males. The injections were given over a period of 13 days, daily except weekends and holidays.
****This group consisted of 20-gram Swiss mice, 16 females and 2 males. The injections were given daily over a period of 21 days, daily except weekends and holidays.

EXAMPLE 3

Effect of 6,6'-Dithiodinicotinic Acid on the Growth of Mice

Swiss albino mice were weaned when about 10 grams of weight. Two groups of 5 mice each were used. The control group received regular mouse chow, pelleted, while the test group received pellets of the same chow containing 4 mg/gram of CPDS. The weight of each group was checked daily for 21 days. At that time the mice weighed about 25 grams each. No difference was found in the rate of growth of the two groups. CPDS thus does not affect the growth of healthy, fast-growing mammals.

EXAMPLE 4

Diethyl Ester of 6,6'-Dithiodinicotinic Acid

Preparation 10 grams of 6-mercaptonicotinic acid (thione) are dissolved in 150 ml of absolute ethanol, 2 ml of concentrated sulfuric acid are added and the mixture is refluxed 4 hours on the steam bath. The ethanol is evaporated under reduced pressure, the resulting oil dissolved in 350 ml of diethyl ether; this solution is washed with a cold aqueous saturated solution of sodium bicarbonate, then dried with magnesium sulfate (anhydrous), filtered, the ether evaporated. A low-melting solid is obtained. This product is dissolved in 2 liters of boiling water, treated with a solution of iodine in aqueous potassium iodide until the color persists. The resulting mixture is allowed to cool in a refrigerator, then the precipitate is collected and recrystallized from ethanol. Yield: 2.5 grams. Melting point: 137°–138° C. Elemental analysis: carbon and hydrogen in agreement with formula.

Properties

Ultraviolet spectra were determined in absolute ethanol.

Ethyl ester of 6-mercaptonicotinic acid thione:

$\lambda_{max}=330$ m$\mu$, $E_{molar}=2.1\times 10^4$

Diethyl ester of 6,6'-dithiodinicotinic acid:

$\lambda_{max}=260$ m$\mu$, $E_{molar}=2.1\times 10^4$ $\lambda_{max}=294$ m$\mu$, $E_{molar}=2.4\times 10^4$ Addition of an excess of mercaptoethanol to a solution of the disulfide causes the UV spectrum to shift to that of the thione, showing that the compound is a thione-forming disulfide.

Toxicity

When administered as an aqueous or oily (sesame oil) suspension subcutaneously to Swiss mice, the compound, which is quite insoluble in water, did not spread systemically, but tended to incapsulate in situ.

When mixed with powdered mouse chow no toxicity was found, as indicated in Table 9.

TABLE 9

Oral Administration of Diethyl Ester of 6,6'-Dithiodinicotinic Acid to mice.

| Group | N° Mice | Conc. in food | Daily Dose per mouse | Daily Dose per kilo | Duration (days) | Visible Effects |
|---|---|---|---|---|---|---|
| 1 | 25 | 4 mg/g | 12 mg | 600 mg | 8 | None |
| 2 | 25 | 6 mg/g | 18 mg | 900 mg | 8 | None |

EXAMPLE 5

4-Carboxypyrimidine-2-Disulfide.(AX-116)

Preparation

As described in the literature.

Properties

The ultraviolet spectrum of the disulfide and that of the corresponding thione (2-mercapto-4-carboxypyrimidine) were determined in aqueous solution of NaHCO$_3$:

4-carboxypyrimidine-2-disulfide:

$\lambda_{max}=240$ m$\mu$, $E_{molar}=2.34\times 10^4$ (pH=7.5)

2-mercapto-4-carboxypyrimidine (thione):

$\lambda_{max}=280$ m$\mu$, $E_{molar}=1.62\times 10^4$ (pH=6.4)

Addition of an excess of cysteine to a solution of the disulfide gave rise to the spectrum of the thione, showing that the disulfide is thione-forming.

Toxicity (a) Intraperitoneal Administration. Solutions were prepared by dissolving the disulfide in aqueous sodium bicarbonate (0.6 g bicarbonate/g disulfide). 6 groups of Swiss (Webster) mice (6 mice per group), were used. Mouse weights were 18–21 g. The disulfide was injected intraperitoneally. The schedule is described in Table 10:

TABLE 10

Injection of 4-carboxypyrimidine-2-disulfide to Mice.

| Group | Injection of | N° Injections |
| --- | --- | --- |
| 1 | 0.1 ml distilled water | 1 daily/5 days |
| 2 | 100 mg/kilo in 0.1 ml | 1 daily/5 days |
| 3 | 500 mg/kilo in 0.1 ml | 1 daily/5 days |
| 4 | 1000 mg/kilo in 0.1 ml | 1 only |
| 5 | 1000 mg/kilo in 0.1 ml | 1 only |
| 6 | 1000 mg/kilo in 0.2 ml | 1 only |

Groups 1, 2 and 3 appeared normal after 5 daily injections. In groups 4 and 5, 6 mice died 24 to 36 hours after injection; the other mice of these groups showed toxic effects but recovered. In group 6, one mouse died about 24 hours after initial injection. After 2 injections (third day) a second mouse died and the survivors were so weak that they could not move, and were sacrificed for autopsy.

Autopsies were carried out on 11 mice:
- 7 mice had enlarged lymph nodes (slightly to moderately)
- 8 mice had inflamed small intestines (slightly to severely)
- 4 mice had inflamed large intestines (slightly to moderately)
- 7 mice had inflamed lungs (slightly to moderately).

It is concluded that, when injected intraperitoneally, AX-116 is non-toxic at doses up to about 500 mg/kilo. Higher doses are toxic, especially to the small intestine.

(b) Oral Administration. AX-116 was mixed with powdered mouse chow. The mice used were Swiss Webster, 18–20 grams each. The results are reported in Table 11:

TABLE 11

Oral Administration of 4-carboxypyrimidine-2-disulfide to Mice.

| Group | N° Mice | Conc. in food | Daily dose per mouse | Daily dose per kilo | Duration (days) |
| --- | --- | --- | --- | --- | --- |
| 1 | 25 | 4 mg/g | 12 mg | 600 mg | 8 |
| 2 | 25 | 6 mg/g | 18 mg | 900 mg | 8 |

No toxic effects were observed in either group, at the oral doses used.

EXAMPLE 6

Diethyl 2,2'-Dithiobis-4-thiazole carboxylate (DRG-49)

Preparation

By a modification of a published procedure.

Properties

The ultraviolet spectrum of the disulfide in absolute ethanol has an absorption maximum at 249 m$\mu$, $E_{249} = 1.2 \times 10^4$. The thione (ethyl-2-mercapto-4-thiazole carboxylate) has an absorption maximum at 305 m$\mu$, $E_{305} = 1.3 \times 10^4$. Upon addition of an excess of a thiol (cysteine) to an ethanol solution of the disulfide, the absorption maximum at 249 m$\mu$ disappears, and a new maximum appears at 305 m$\mu$, this being the spectrum of the thione. This shows that DRG-49 is a thione-forming disulfide.

Toxicity

Twenty female mice C57BL/6J received a daily dose of 800 mg/kilo orally, the drug being mixed with powdered mouse chow (4 mg/gram chow).

Administration was continued for
- 22 days in 5 mice
- 32 days in 15 mice

No deaths occurred, and no toxic symptoms were noticed. The mice were healthy and lively at the end of the period.

EXAMPLE 7

Human Administration of 6,6'-Dithiodinicotinic Acid (CPDS)

(a) CPDS was administered orally to a healthy, 48-year-old woman, with the following schedule:

Day 1—
  10 AM, 600 mg
  10 PM, 600 mg
Day 2— 10 AM, 600 mg
Day 3— 10 AM, 300 mg
Day 4— 10 AM, 300 mg
Day 6— 10 AM, 150 mg

Blood analyses were performed on Day 0, before beginning the a administration of the compound, and on Day 3, two hours after taking the compound. The following determinations were carried out in the blood: glucose, urea nitrogen, uric acid, cholesterol, calcium, total bilirubin, potassium, sodium, alkaline phosphatase, total protein, albumin, globulin, A/G ratio, phosphorus, serum glutamic-oxalacetic transaminase, lactate dehydrogenase, serum glutamate-pyruvate transaminase.

All these values were found to be normal both on Day 0 and on Day 3, showing that administration of CPDS had not affected them. Blood counts and morphology, as well as urine analysis, gave normal results. Physical examination by a physician revealed no harmful effects.

(b) CPDS was administered orally to a healthy, 56-year-old man, with the same schedule as above. The same analysis were performed, and no changes were found. Physical examination revealed no harmful effects.

EXAMPLE 8

Human Administration of 6,6'-Dithiodinicotinic Acid Diethyl Ester 6,6'-Dithiodinicotinic acid diethyl ester (150 mg) was administered orally to a 48-year-old healthy woman. No adverse effects were observed.

EXAMPLE 9

Human Administration of Diethyl 2,2'-Dithiobis-(4-Thiazole-Carboxylate) (DRG-49)

(a) The compound was administered orally to a healthy 56-year-old man, with the following schedule:

Day 1–8—
  10 AM, 60 mg
  10 PM, 60 mg
Day 9–16—
  10 AM, 150 mg

10 PM, 150 mg

Blood and urine samples were taken as follows: Day 0, Day 8, and Day 16. The determinations performed were the same as listed in Example 22. No significant changes were found after administration of the compound.

(b) The compound was administered orally to a healthy 48-year-old woman, with the same schedule as above. Blood and urine samples were taken at the same times as above, and the same determinations performed. No significant differences were found after administration of the compound.

EXAMPLE 10

Treatment of Cancer Patient

E.P., female, 50 years old. Diagnosis; probable thyroid neoplasia with related lymph node metastases. Hemithyroidectomy was performed and neck lymph nodes dissected. Administration of CPDS was begun 3 months after surgery ($3 \times 300$ mg per day, orally), and has been continued for about two months. Soon after beginning CPDS treatment, an increase of well-being and activity was noticed, as well as an improvement of the patient's general condition, and an increase of body weight.

EXAMPLE 11

Treatment of Cancer Patient

S.M., 57 year old woman. Diagnosis: anaplastic carcinoma of left lung. Left pneumonectomy was performed 20 months ago. Administration of CPDS was begun on the 10th post-operatory day, at an oral dose of $3 \times 225$ mg/day, and continued for 30 days. No treatment for the following 6 months, then two months of treatment at the same dose, then four months without treatment; then the treatment was started again at $4 \times 225$ mg/day, orally, and is currently being continued at this dose. At the time of writing, 20 months after surgery, the patient is in excellent physical and psychological conditions. All the laboratory tests are negative; they include X rays, hematologic tests, hemocrome, azotemia, glycemia, alkaline phosphatase, transaminase and CEA. It should be noted that two other patients with the same diagnosis who underwent surgery at the same time, but who did not receive CPDS treatment, are deceased. In this patient an increased appetite was also caused by this treatment, which is being continued.

EXAMPLE 12

Treatment of Cancer Patient

C. V., 55-year-old man. Diagnosis: adenocarcinoma of left lung. An exploratory thoracotomy was performed: metastases at the hylum lymph nodes were found. The tumor was therefore inoperable and the patient was "opened and closed". Before surgery the patient had had several hemophthysis episodes, and he had two more after surgery. CPDS treatment ($3 \times 300$ mg/day, orally) was started 5 days before surgery, and continued for 40 days after surgery. During this treatment the pain at the left shoulder disappeared, and there were no further hemophthysis episodes. CPDS treatment was discontinued for 6 months. After this time, at a check-up visit, the patient complained again of left shoulder pain, and of further hemophthysis episodes. CPDS treatment was instituted again ($3 \times 300$ mg/day, orally): the shoulder pain disappeared after a few days, and there have been no further hemophthysis episodes. The patient is alive, well and active after 15 months. It should be noted that the patient received no surgical therapy (since the surgery was only exploratory) nor chemotherapy or radiation therapy. The only treatment he received was CPDS; its beneficial effects appear evident. In this case, as in others, the absence of undesirable side-effects was confirmed, and the standard clinical laboratory values were all normal. The tests performed are those listed in the previous Example.

EXAMPLE 13

Treatment of Cancer Patient

Z. C., 39 year old man. Diagnosis: epidermoid carcinoma of right lung. Upper lobectomy was performed 6 months ago. Administration of 6,6'-dithiodinicotinic acid was begun on the third post-operatory day ($3 \times 225$ mg/day, orally) and is being continued without interruptions. The patient was depressed and without energy. After CPDS treatment was begun, he became lively and extroverted, his appetite has improved, and his body weight has increased. All the standard clinical laboratory tests are negative; they include X-rays, blood tests, alkaline phosphatase, azotemia, glycemia, transaminase, CEA. This patient received no chemotherapy or radiotherapy; he went back to his usual occupation, and has no physical complaints.

EXAMPLE 14

Treatment of Cancer Patient

D. P., 65 year old man. Five years ago he suffered a left submandibulary tumefaction (salivary gland); a biopsy showed that it was an undifferentiated neoplasia. Left cervical dissection was performed and the gland removed; this was followed by radiation therapy and chemotherapy. The patient remained asymptomatic for 5 years.

Three months ago a tumefaction appeared at the edge of the submandibular scar. A biopsy showed that it was a metastasis of an undifferentiated tumor. A right submandibulary dissection was performed. CPDS treatment was begun 30 days after surgery, and is being given daily without interruptions ($3 \times 300$ mg/day, orally). At the same time, chemotherapy treatment is also given. All the standard laboratory tests are negative; they include chest X-rays, bone X-rays, total body scan, CEA. The following was observed after CPDS treatment was begun: improvement of appetite, improvement of the psychological state of the patient, who was emotional and depressed. The patient is in good condition and is continuing CPDS treatment.

EXAMPLE 15

Treatment of Cancer Patient

A woman, age 53, following surgery for advanced ovarian carcinoma, was given chemotherapy treatment. Concurrently and subsequently she took CPDS orally ($2 \times 250$ mg/day) until her death after approximately three months. At the time when treatment of this patient was commenced, she was in the terminal stages of cancer, but the treatment relieved her of her deep depression, gave her an increased sense of well-being, which persisted until her death.

EXAMPLE 16

Treatment of Cancer Patient

A male cancer patient, age 69, suffering from small cell carcinoma of the lungs, was treated with CPDS (2×300 mg/day, orally), alternating at first with conventional chemotherapy. According to the generally accepted data, the life expectancy for patients with this tumor is less than about 4 months if untreated, up to one year with standard chemotherapy. This patient lived for 19 months after diagnosis and, since taking CPDS, experienced an increase in appetite (he previously was anorexic), of well-being and activity, and had resumed his usual professional activity, part-time.

EXAMPLE 17

Treatment of Cancer Patient

C. G., 69 year old man with prostatic carcinoma diagnosed 7 years ago. At the time of diagnosis, surgical treatment was performed. The patient had extended bone metastases, which caused severe pain and debilitated and incapacitated him. After CPDS treatment was begun (3×300 mg/day, orally), the pains decreased, his a appetite improved, and he was again able to be relatively active. The patient moved away, so it was not possible to further follow the course of his disease.

EXAMPLE 18

Treatment of Cancer Patient

T. S., 67 year old woman with uterus carcinoma diagnosed and treated surgically 5 years previously. After CPDS treatment was begun (3×300 mg/day, orally), her general state improved, the pains decreased, and she was able to become relatively active. After 6 months of CPDS treatment, the patient moved away, and it was not possible to further follow the course of her disease.

While conventional chemotherapy is usually given in relatively short cycles alternated with rest periods, because of its toxicity, 6,6'-dithiodinicotinic acid can be given daily for indefinite periods of time, not only without toxic effects, but with enhanced sense of well-being, and increased appetite.

The dosage rate of the dicyclic or other reagents to be employed in the practice of this invention can be varied within wide limits and still be effective for the intended purpose. In general, however, good results can be obtained in the several areas of utility by administering the reagent in amounts calculated to maintain a concentration in blood of $10^{-9}$ molar to $10^{-3}$ molar.

For example, a possible use of 6,6'-dithiodinicotinic acid herein described consists in the administration of adequate doses at the time of surgery for cancer. It is known that manipulation of a tumor during surgery causes large numbers of cancer cells to enter the blood stream with concomitant high danger of formation of metastases. Treatment with the reagent should be continued for an adequate period of time both before and following surgery until the natural defenses of the organism have destroyed the remaining circulating cancer cells.

The dicyclic or other reagents employed in a practice of this invention to react preferentially with peripheral —SH groups of cells can be administered to living mammals in any desired fashion such, for example, as by injection into the blood stream or into muscle or body tissue. Oral administration is also effective. The chemical can be employed alone or along with an oleaginous or other vehicle which will slow down its rate of absorption into the system. It is also possible to use a reagent of the foregoing character which is prepared in radioactive form by incorporating one or more radioactive carbon, sulfur or tritium atoms. By use of this practice, the efficiency and efficacy of the radioactive elements are greatly enhanced inasmuch as they become chemically bonded to the cells for the desired interval.

I claim:

1. The method of lessening the pains and increasing the well-being of patients with carcinomas or undifferentiated neoplasias, which comprises administering to said patients, after surgery, an effective amount of a compound having a structure

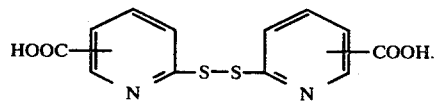

2. The method of lessening the pains and increasing the well-being of patients with carcinomas or undifferentiated neoplasias, which comprises administering to said patients, after surgery, an effective amount of 6,6'-dithiodinicotinic acid.

3. The method of treating carcinoma patients after surgery for carcinoma to lessen pain, induce a feeling of well-being and increase appetite which comprises orally administering to the patients an effective amount of 6,6'-dithiodinicotinic acid.

4. The method of claim 3 wherein the amount of 6,6'-dithiodinicotinic acid administered is adapted to maintain a concentration in the range of $10^{-9}$ to $10^{-3}$ molar in the blood of the patient.

5. The method of claim 3 wherein the amount of dithiodinicotinic acid administered is in the range about 500 to about 900 mg per day.

* * * * *